(12) United States Patent
Benndorf et al.

(10) Patent No.: US 8,676,297 B2
(45) Date of Patent: Mar. 18, 2014

(54) METHOD AND DEVICE FOR SEPARATE THREE-DIMENSIONAL PRESENTATION OF ARTERIES AND VEINS IN A PART OF BODY

(75) Inventors: Goetz Benndorf, Houston, TX (US); Klaus Klingenbeck-Regn, Nürnberg (DE); Michael Zellerhoff, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 1938 days.

(21) Appl. No.: 11/724,657

(22) Filed: Mar. 15, 2007

(65) Prior Publication Data

US 2007/0232901 A1 Oct. 4, 2007

(30) Foreign Application Priority Data

Mar. 16, 2006 (DE) .......................... 10 2006 012 181

(51) Int. Cl.
*A61B 5/05* (2006.01)

(52) U.S. Cl.
USPC .......................................................... 600/425

(58) Field of Classification Search
USPC .......................................................... 600/425
See application file for complete search history.

(56) References Cited

U.S. PATENT DOCUMENTS

| | | | | |
|---|---|---|---|---|
| 5,256,394 | A * | 10/1993 | Spielvogel | 424/9.4 |
| 6,377,835 | B1 * | 4/2002 | Schoenberg et al. | 600/419 |
| 2005/0283066 | A1 | 12/2005 | Yamada | |

FOREIGN PATENT DOCUMENTS

| | | |
|---|---|---|
| DE | 19711170 U1 | 10/1997 |
| DE | 10356325 A1 | 6/2004 |
| JP | 63242236 A | 10/1988 |
| JP | 9327454 A | 12/1997 |
| JP | 2003126074 A | 5/2003 |
| JP | 2003164445 A | 6/2003 |
| JP | 2006034952 A | 2/2006 |
| WO | WO 2005044107 A1 | 5/2005 |

OTHER PUBLICATIONS

K.Wiesent, K. Barth, N. Navab, P. Durlak, T. Brunner, O. Schuetz and W. Seissler, "Enhanced 3-D-Reconstruction Algorithm for C-Arm Systems Suitable for Interventional Procedures", IEEE Transactions on Medical Imaging, vol. 19, No. 5, May 2000, pp. 391-403.
Communication from Japanese Patent Office, Feb. 28, 2012, pp. 1-5.

* cited by examiner

*Primary Examiner* — Tse Chen
*Assistant Examiner* — Hien Nguyen

(57) ABSTRACT

The invention is directed to a method and a device for separate three-dimensional presentation of arteries and/or veins of a vessel system in a part of the body of a vertebrate by a rotation computer tomography. A masking run of the tomograph is undertaken without contrast media around the part of the body. Then two filling runs with contrast media are executed, with the venous phase of vessel contrasting during the first filling run occurring during the arterial phase of vessel contrasting of the second filling run and vice-versa. The data from the first and second filling run is combined into data sets from the arterial or the venous phases of the vessel contrasting of the filling runs. The data of the masking run is subtracted from the combined data sets to obtain final data sets for a three-dimensional presentation of the arterial or the venous vessel system.

7 Claims, 2 Drawing Sheets

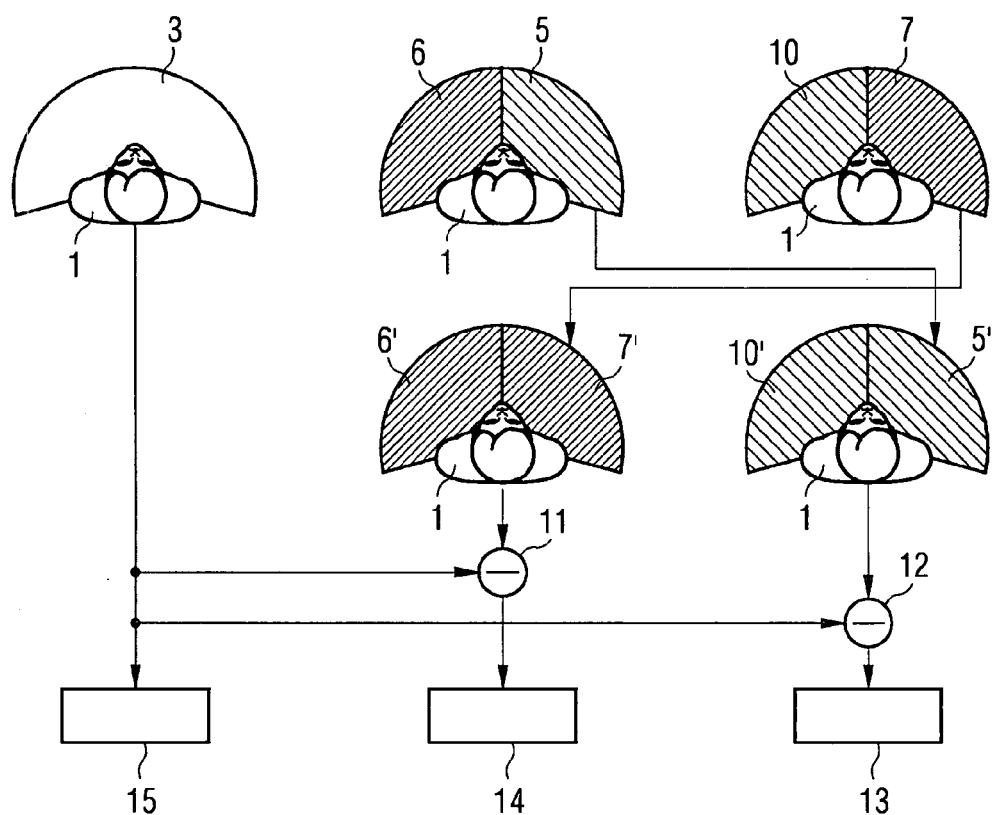

_US 8,676,297 B2_

METHOD AND DEVICE FOR SEPARATE THREE-DIMENSIONAL PRESENTATION OF ARTERIES AND VEINS IN A PART OF BODY

CROSS REFERENCE TO RELATED APPLICATIONS

This application claims priority of German application No. 10 2006 012 181.3 filed Mar. 16, 2006, which is incorporated by reference herein in its entirety.

FIELD OF THE INVENTION

The present invention relates to a method for separate three-dimensional presentation of arteries and/or veins of a vessel system in a part of the body of a vertebrate by means of a rotation computer tomograph as well as a device, especially for execution of the method. Preferred applications of the invention are for C-arm angiographs.

BACKGROUND OF THE INVENTION

There is a growing demand for the most accurate possible three-dimensional presentation of the appearance and course of vessels in parts of the body, especially of arteries and veins, for diagnostic purposes in the field of vessel diseases and their treatment. The examination of cerebral aneurysms represents an important area of application, which also includes an analysis and optimum presentation for definition of the aneurysm neck under topographical relationships to adjacent vessels. Angiographies are also performed on other parts of the body in order to identify arteriosclerotic changes or malformations. The introduction of computer-aided rotation angiography, which reconstructs three-dimensional presentations with an even resolution from the raw projection data achieved a technical breakthrough in the field of diagnostics. Prior art in this case are what are known as C-arm-angiographs, in which an x-ray source and a sensor arranged opposite this source are rotated in an approximately 200° arc around the part of a patient's body to be examined and between 50 and 500 x-ray images are recorded and digitally stored during this process. Projection x-ray images recorded from different angles of projection can then be computed into a three-dimensional model of the x-rayed part of the body. However, with conventional 3D angiography it is not possible to make a sufficiently clear distinction between arterial and venous vessel system because of the recording times and the dynamics of the contrast medium propagation.

With the previously known three-dimensional vessel presentation what are known as a masking run and a filling run are recorded. In the masking run the C-arm is rotated around the part of the patient's body or around the entire patient and the x-ray images are recorded over the predetermined angular range. Contrast media is then injected into the vessel of interest and a second set of x-ray images is recorded with a new C-arm rotation, mapping what is known as the filling run. The models of the two sequences of images are now subtracted from one another so that only the contrasted vessels (i.e. those containing contrast media) are still visible in the result. These are now reconstructed using a 3D reconstruction method into a three-dimensional data set. Alternatively masking and filling run can also be reconstructed separately and the resulting three-dimensional data sets subtracted from each other.

The 3D angiography method according to the prior art as a rule delivers a three-dimensional data set which represents both a part of the arterial and also parts of the venous vessel system. The reason for this deficiency of current angiography systems can be found in the fact that the rotation time of the tomograph, at appr. 5 secs, is far longer than what is referred to as the arterial phase of the vessel contrasting, which only lasts 2 to 3 secs. Thereafter the contrast media migrates via the usual capillary paths into the venous vessel system, so that, after the execution of the arterial phase, a venous phase shows the vessel contrasting which will recorded in a later part of the rotation of the tomograph, so that a three-dimensional mixed structure made up of arteries and veins is produced.

SUMMARY OF THE INVENTION

The underlying object of the present invention is thus to find an approach to creating three-dimensional data sets of vessels which represents either arteries only or veins only (as desired).

In accordance with the invention this object is achieved by the method for separate three-dimensional presentation of arteries and/or veins as well as by the apparatus for separate three-dimensional presentation according to the independent claims.

Further advantageous embodiments, aspects and details of the present invention emerge from the dependent claims, the description and the enclosed drawings.

The idea underlying the invention is to execute more than one filling run and to stagger these in time in relation to the contrast injection so that all parts of the imaged part of the body are imaged at least once in the arterial phase of the vessel contrasting to make a three-dimensional reconstruction possible.

In a first aspect the invention is thus directed to a method for separate three-dimensional presentation of arteries and/or veins of a vessel system in a part of the body of a vertebrate by means of a rotation computer tomograph, with the method having the following steps:

(a) Executing a masking run of the tomograph without contrast media around the part of the body to be examined;

(b) Executing a first filling run of the tomograph around the part of the body using a contrast medium, with a first part of the filing run taking place during an arterial phase of vessel contrasting and a second part during the venous phase of vessel contrasting;

(c) Executing at least one second filling run of the tomograph around the part of the body at such a time relative to the injection of further contrast media that that part of the second filling which occurs in the first filling run during the venous phase of the vessel contrasting occurs during the arterial phase(s) of the vessel contrasting of the at least one second filling run and vice-versa;

(d) Combining the data from the first and at least one second filling run into a first data set containing the combined data from the arterial phase of the vessel contrasting of the first and second filling runs and/or into a second data set containing the combined data from the venous phases of vessel contrasting of the first and second filling runs; and (e) Subtraction of the data set obtained during the masking run from the first and/or second data sets obtained during the combination, in order to obtain at least one final data set which contains data for a three-dimensional presentation of the arterial or venous vessel system.

In this case a rotation computer tomograph is taken to mean any imaging method based on a penetration technique with computation of a three-dimensional model of the examined object.

A masking run in the sense of the present invention is the rotation computer tomograph run without the use of a contrast medium.

A contrast medium, as is familiar to those skilled in the art, is a substance which is opaque for the relevant imaging method, for example for x-ray beams, and thereby records images of filled-out pole structures through a marked x-ray shadow.

A filling run in accordance with the invention is to be seen as a run of the tomograph in which the hollow space to be examined, in this case vessels, is filled with contrast medium up to the level at which a suitable contrast is produced in the imaging method.

An injection of contrast media is to be understood as introducing the contrast medium into the hollow space to be examined or the vessel to be examined, by means of a syringe for example.

Combining the data from the filling runs into data sets is to be understood as combining, with the aid of a predetermined algorithm and where necessary with the aid of a human evaluation, subsets of the data of the individual filling runs into a new data set according to predetermined rules. In accordance with the invention the data is selected so that it is complementary and so that data is present over the entire scanning arc of the tomograph used, i.e. from all positions at which projection images will be recorded, which belongs either to the arterial phase of vessel contrasting or to the venous phase.

A subtraction of data sets is, in accordance with normal usage of this expression by those skilled in the art for tomographic methods, to be understood as a computational procedure in which the measurement data of a background is subtracted from the measurement data of interest so that essentially only the measurement data of interest remains in the data set.

To generate a three-dimensional model from the projection image data of the individual images of the runs, a method is used which is referred to in the angiography field as reconstruction. Such a reconstruction of data sets into three-dimensional data sets can be executed at different points of the inventive method, which means before the combination of the data, before the subtraction of the data sets and after its combination or also after the subtraction on the final data set, with different considerations as regards the complexity of the conversion and the already available mechanisms of the computer tomographs used for executing the method being taken into account.

In a preferred embodiment the part of the body examined is a person's cranium. An important area of application in this case is the detection of aneurysms in the vessels of the brain. It goes without saying however that other parts of the body of human beings and other types of animal with a vessel system are basically accessible using the inventive method. The inventive method has been restricted to vertebrates since these have a separate arterial and venous blood circulation, but it goes without saying that where necessary the method can also be applied to other classes of animal, provided they have a contrastable vessel system with arteries and veins.

In a preferred embodiment of the invention only two filling runs are undertaken, provided these are sufficient to correctly represent all angles of view and thereby all areas of the examined parts of the body and to represent the arterial and venous vessels separately. In an alternate embodiment as many filling runs are performed as required to obtain data both from the venous phase of the vessel contrasting and also data from the arterial phase of the vessel contrasting from all parts of the runs. This can for example be necessary with tomographs which have a far longer run time for one run than the arterial phase of vessel contrasting, so that three or even more filling runs must be made before all perspectives are covered.

Various basic technologies are available for implementation of the rotation computer tomograph. Thus, in one preferred embodiment, it is a rotation x-ray computer tomograph, such as a C-arm angiograph. In another preferred embodiment the rotation computer tomograph is an ultrasound tomograph, and in a further preferred embodiment the rotation computer tomograph is a nuclear resonance tomograph. It goes without saying that the contrast medium used in each case depends on the technology to be used, since the excitations and waves to be employed have different effects on substances in each case.

Depending on the computer tomograph used and its pattern of movement, in a preferred embodiment of the invention the first and the at least one second filling run are performed in the same scanning direction, with the first filling run being started at the time of a contrast medium injection with vessels to be examined (or to put it differently the contrast medium is injected directly before or at the start of the filling run) and the second filling run being started so that, at the time of a further contrast medium injection, a part of the second filling run has already taken place (or the contrast medium injection takes place somewhere in the middle of the filling run and preferably precisely in the middle of the filling run at two thirds, or at one third and/or two thirds for two further second filling runs).

For computer tomographs which can change the direction of scanning the inventive method can also be embodied so that the first and the at least one second filling run are performed in different scanning directions, with the first filling run being started at the time of a contrast medium injection in the vessels to be examined, and at least one second filling run being started at the time of a further contrast medium injection. In this embodiment a first filling run and a second filling run are basically necessary, but it goes without saying that more than two filling runs, again with corresponding staged contrast medium injections can be executed.

In a further aspect the invention is directed towards an apparatus, with all that has been stated in relation to the method also applying to the apparatus or vice versa, so that each refers to the other. The inventive apparatus for separate three-dimensional presentation of arteries and/or veins of a vessel system in a part of the body of a vertebrate comprises a rotation computer tomograph with (a) A first data memory for storing the data obtained during a masking run and during at least a first and a second filling run of the rotation computer tomograph;

(b) A first computation module for combining the data from the first and at least a second filling run into a first data set containing combined data from arterial phases of the vessel contrasting of the first and second filling runs and/or into a second data set containing the combined data from venous phases of the vessel contrasting of the first and second filling runs;

(c) A further measurement data memory for storing the first and/or second data set; and (d) A second computation module for subtraction of the data obtained during the masking run from the first and/or second data sets obtained during the combination, in order to obtain at least one final data set containing data for a three-dimensional presentation of the arterial or of the venous vessel system.

A computation module in this case is to be understood either as a facility specifically designed to perform the calculations to be undertaken, for example an analog computer or a digital signal processor with a corresponding control, or a computation module is to be understood as a software computer program product which implements the functionalities on a universal computing system. A data memory is to be understood as any device able to store digital data, be it a volatile memory or a permanent main memory, a hard disk, an optical data medium, etc., with this memory being able to be accessed by the computation modules.

In an especially preferred embodiment the apparatus is suitable for executing the inventive method.

The computer tomograph, as a component of the inventive apparatus, can be a rotation x-ray computer tomograph such as a C-arm angiograph, an ultrasound tomograph or also a nuclear resonance tomograph.

BRIEF DESCRIPTION OF THE DRAWINGS

The invention will be explained below in greater detail on the basis of practical exemplary embodiments which refer to the enclosed drawings, which are as follows:

FIG. 3 shows the method for determining final data sets from the raw data obtained by scanning.

DETAILED DESCRIPTION OF THE INVENTION

Figure 1:
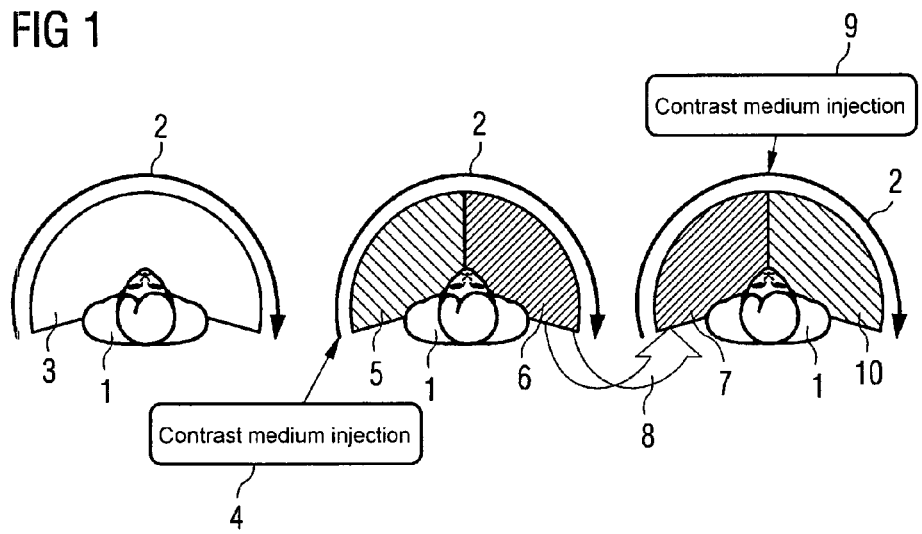
FIG. 1 shows the principle of scanning a patient's body in a first embodiment of the invention.

FIG. 1 describes the inventive method when using a C-arm angiograph which can only perform scanning runs in one direction.

The left-hand part of FIG. 1 shows a body positioned for examination, such as a patient 1, in cross-section, arrow 2 shows the direction of scanning of the C-arm angiograph used and sector 3 shows the detected projection angle of the masking run. Here the entire part of the body is recorded and represented in accordance with the options provided by the angiograph used. The middle part of FIG. 1 shows the first filling run, in which, at the beginning of the second scanning run in the same scanning direction 2, a contrast medium is injected into or adjacent to the vessel to be examined. FIG. 1 illustrates the point in time of the contrast medium injection 4. The cross-hatched area 5 is the area of the filling run, in which the arterial phase of the vessel contrasting occurs. After the end of this phase 5, during which the contrast medium has reached the venous areas of the vessel system, the C-arm angiograph is only still able to record the venous phase of vessel contrasting, represented by the cross-hatched area 6, with enhanced contrast. In the right-hand part of the figure the second filling run is shown, in which once again in the same direction of scanning 2 and following on directly from the first filling run for the area of the run which represented the arterial phase during the first filling run, the venous phase 7 of the vessel contrasting is recorded, since, as shown by the arrow 8, the venous phase of the vessel contrasting extends into the second filling run. In roughly the middle of the second filling run a new contrast injection 9 takes place, so that shortly afterwards an arterial phase of vessel contrasting 10 begins, covering the area of the filling run which belonged in the first run to the venous phase of vessel contrasting. Thus in the example given here both arterial contrasting and venous contrasting can be represented by two filling runs of the entire C-arm.

It should be ensured in each case that immediately after the rotation of the first filling run, the C-arm is returned and the second filling run undertaken. Since the venous phase is as a rule far longer than the arterial phase the veins are still sufficiently contrasted at this point.

Figure 2:
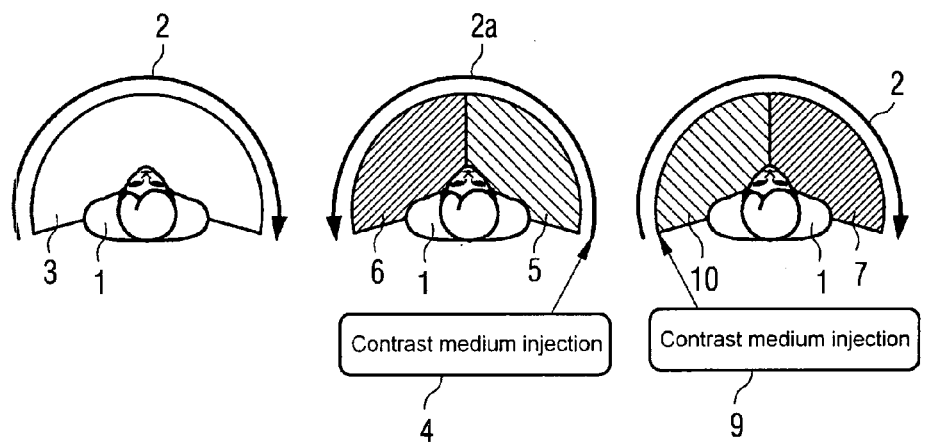
FIG. 2 shows the principle of scanning a patient's body in a second embodiment of the invention.

For systems which allow images to be recorded in both directions, a different protocol is recommended, as is shown in FIG. 2. In FIG. 2 the same reference symbols correspond to the same or similar objects. The masking run is performed here as in the embodiment shown in FIG. 1. Following on from this, the first filling run is now started with reversed rotation or scanning direction 2a and with injection of a contrast medium 4. The contrast medium injection is triggered relative to the start of the rotation such that the first half of the rotation 5 produces arterial contrasting and the second half 6 venous contrasting. The second filling run is undertaken in the right-hand part of FIG. 2 in entirely the same manner as the first filling run but once again with the opposite direction of rotation 2a. Since the recording of the venous phases of the first filling run is followed directly by the arterial phase 10 of the second filling run, a certain interval must be maintained between the runs until the contrast medium has been flushed out of the veins in order to avoid double arterial/venous contrasting.

FIG. 3 shows the general procedures for combination and subtraction of the data obtained in the different runs. The same reference symbols once again identify the same processes or objects in this figure. Here the data of the arterial phase 5 and of the venous phase 6 of the first filling run, as well as of the arterial phase 10 and of the venous phase 7 of the second filling run, is combined in such a way as to produce two new data sets, of which one is made up of the venous phase 6 of the first filling run as well as the venous phase 7 of the second filling run, and the second of the arterial phase 5 of the first filling run and of the arterial phase 10 of the second filling run. By subsequent subtraction of the masking run in 11 and 12 and reconstruction into a three-dimensional data set, two three-dimensional data sets are obtained, of which one contains a presentation of the arterial vessel system 13 and another a presentation 14 of the venous vessel system. The reconstruction of the masking run also allows a presentation 15 of the surrounding tissue (low-contrast presentation) to be obtained. The inventive method makes it possible to present the arterial vessel system, the venous vessel system and the surrounding tissue in three dimensions, as shown in FIG. 3. Since only half of the images of the arterial phase have to be recorded in each of the two filling runs, only half of the recording time is also devoted to the arterial phase. This condition is able to be fulfilled with an arterial phase of 2 to 3 secs and a current minimum recording time per rotation of 5 seconds, which makes a separate, overlay-free presentation of the arteries and veins possible.

The invention claimed is:

1. A method for generating a data set of an artery of a vessel system in a part of a body of a vertebrate with a rotation computer tomograph, comprising:
    performing a masking run by the tomograph without an injection of contrast media around the part of the body;
    recording data of the masking run in a first scan over a defined scanning arc;
    performing a first filling run with the tomograph with a first injection of the contrast media around the part of the body, the first filling run comprising an arterial phase part and a venous phase part;
    recording, in a second scan over the defined scanning arc, data of the arterial phase of vessel contrasting during the first filling run;
    performing a second filling run with the tomograph with a second injection of the contrast medium around the part of the body, the second filling run comprising an arterial phase part and a venous phase part;

recording, in a third scan over the defined scanning arc, data of the arterial phase of vessel contrasting of the second filling run;

combining the data of the arterial phase of vessel contrasting of the first filling run and the data of the arterial phase of vessel contrasting of the second filling run into a combined data set of artery so that arterial phase data of vessel contrasting is provided over the entire defined scanning arc;

subtracting the data of the masking run from the combined data set of artery to generate the data set of the artery of the vessel system; and using the data set of the artery of the vessel system for human observation, wherein the first and the second filling runs are performed in different scanning arcs, wherein the first injection of the contrast medium is injected when the first filling run starts and the second injection of the contrast medium is injected when the second filling run starts, and wherein the second filling run starts when the contrast medium in the first filling run has been flushed out of veins of the vessel system, wherein the method further comprising:

recording data of a venous phase of vessel contrasting of the first filling run during the venous phase part of the first filling run, recording data of a venous phase of vessel contrasting of the second filling run during the venous phase part of the second filling run, combining the data of the venous phase of vessel contrasting of the first filling run and the data of the venous phase of vessel contrasting of the second filling run into a further combined data set of veins so that venous phase data of vessel contrasting is provided over the entire defined scanning arc, and subtracting the data of the masking run from the further combined data set to generate a data set of a vein of the vessel system, wherein the recited steps include reconstructing a three-dimensional data set from data selected from the group consisting of: the data of the masking run, the data of the arterial phase of vessel contrasting of the first filling run, the data of the venous phase of vessel contrasting of the first filling run, the data of the arterial phase of vessel contrasting of the second filling run, the data of the venous phase of vessel contrasting of the second filling run, the combined data set of artery, the further combined data set of veins, the data set of the artery of the vessel system, and the data set of the vein of the vessel system.

2. The method as claimed in claim 1, wherein the part of the body is a cranium of the vertebrate.

3. The method as claimed in claim 1, wherein a plurality of first and second additional filling runs are performed to record data from a plurality of additional arterial phases of vessel contrasting and to record data from a plurality of additional venous phases of vessel contrasting.

4. The method as claimed in claim 1, wherein the rotation computer tomograph is selected from the group consisting of: a rotation x-ray computer tomography, an ultrasound tomography, and a nuclear resonance tomograph.

5. The method as claimed in claim 4, wherein the rotation x-ray computer tomograph is a C-arm angiograph.

6. An apparatus for generating an image data set of an artery of a vessel system in a part of a body of a vertebrate, comprising:

a rotation computer tomography apparatus that configured to obtain:
a recording of a masking run during a first scan over a defined scanning arc to provide data for a masking run without an injection of contrast media around the part of the body,
a recording of a first filling run with a first injection of contrast media around the part of the body to record data of an arterial phase of vessel contrasting during a second scan over the defined scanning arc, and
a recording of a second filling run with a second injection of contrast media around the part of the body to record data of an arterial phase of vessel contrasting during a third scan over the defined scanning arc; and a computation device that configured to:
combine the data of the arterial phase of vessel contrasting of the first filling run obtained during the second scan over the defined scanning arc and the data of the arterial phase of vessel contrasting of the second filling run obtained during the third scan over the defined scanning arc into a combined data set of artery, and
subtract the data of the masking run from the combined data set of artery to generate the image data set of the artery of the vessel system, wherein the first and the second filling runs are performed in different scanning arcs, wherein the first injection of the contrast medium is injected when the first filling run starts and the second injection of the contrast medium is injected when the second filling run starts, and wherein the second filling run starts when the contrast medium in the first filling run has been flushed out of veins of the vessel system, wherein the rotation computer tomography apparatus configured to:
record data of a venous phase of vessel contrasting of the first filling run during a venous phase part of the first filling run, and
record data of a venous phase of vessel contrasting of the second filling run during a venous phase part of the second filling run, and wherein the computation device configured to:
combine the data of the venous phase of vessel contrasting of the first filling run and the data of the venous phase of vessel contrasting of the second filling run into a further combined data set of veins, and
subtract the data of the masking run from the further combined data set of veins to generate an image data set of a vein of the vessel system, the apparatus further comprising a data memory that stores data selected from the group consisting of: the data of the masking run, the data of the arterial phase of vessel contrasting of the first filling run, the data of the venous phase of vessel contrasting of the first filling run, the data of the arterial phase of vessel contrasting of the second filling run, the data of the venous phase of vessel contrasting of the second filling run, the combined data set of artery, the further combined data set of veins, the image data set of the artery of the vessel system, and the image data set of the vein of the vessel system.

7. The apparatus as claimed in claim 6, wherein the arterial phase part of the second filling run occurs in the venous phase part of the first filling run and the venous phase part of the second filling run occurs in the arterial phase part of the first filling run.

* * * * *